United States Patent
Bonrath et al.

(10) Patent No.: US 7,153,984 B2
(45) Date of Patent: Dec. 26, 2006

(54) MANUFACTURE OF α-TOCOPHEROL

(75) Inventors: Werner Bonrath, Freiburg (DE); Alois Haas, Kleinmachnow (DE); Simone Hoppmann, Leipzig (DE); Thomas Netscher, Bad Krozingen (DE); Horst Pauling, Aesch (CH)

(73) Assignee: DSM IP Assets B.V., Te Heerlen (NL)

( * ) Notice: Subject to any disclaimer, the term of this patent is extended or adjusted under 35 U.S.C. 154(b) by 50 days.

(21) Appl. No.: 10/535,603

(22) PCT Filed: Sep. 30, 2003

(86) PCT No.: PCT/EP03/10837

§ 371 (c)(1),
(2), (4) Date: May 19, 2005

(87) PCT Pub. No.: WO2004/046127

PCT Pub. Date: Jun. 3, 2004

(65) Prior Publication Data

US 2006/0020139 A1 Jan. 26, 2006

(30) Foreign Application Priority Data

Nov. 21, 2002 (EP) .................. 02025990

(51) Int. Cl.
*C07D 311/72* (2006.01)
(52) U.S. Cl. .................................... 549/411
(58) Field of Classification Search ................ 549/411
See application file for complete search history.

(56) References Cited

U.S. PATENT DOCUMENTS

| 3,082,258 | A | 3/1963 | McConnell et al. |
| 5,900,494 | A | 5/1999 | Bonrath |
| 6,369,242 | B1 | 4/2002 | Bonrath et al. |

FOREIGN PATENT DOCUMENTS

| EP | 0 949 255 A1 | 10/1999 |
| EP | 1 134 218 A1 | 9/2001 |

OTHER PUBLICATIONS

Ishihara, K. et al., "Practical Synthesis of (±)-α-Tocopherol. Trifluoromethanesulfonimide as an Extremely Active Bronsted Acid Catalyst for the Condensation of Trimethylhydroquinone with Isophytol," *Synlett*, vol. 11, pp. 1045-1046 (1996).
Sartori, P. and Jüschke, R., "Verbessertes Verfahren zur Darstellung des tri-Kalium-methantrisulfonat-Monohydrates," *J. Prakt. Chem.*, vol. 336, pp. 373-374 (1994).
Jüschke, R. and Sartori, P., "Untersuchungen zur Säurestärke von Alkanpolysulfonsäuren," *Z. Naturforsch*, vol. 51b, pp. 1691-1700 (1996).
Hall, J.R. et al., "Crystal Structure, and the Infrared and Raman Spectra, of Tripotassium Methanetrisulphonate Hydrate, $K_3[CH(SO_3)_3] \cdot H_2O$," *J.C.S. Dalton*, pp. 149-155 (1980).

*Primary Examiner*—Joseph K. McKane
*Assistant Examiner*—Michael P. Barker
(74) *Attorney, Agent, or Firm*—Bryan Cave LLP

(57) ABSTRACT

A process for the manufacture of (all-rac)-α-tocopherol by the acid-catalyzed reaction of trimethylhydroquinone with isophytol or phytol is characterized by carrying out the reaction in the presence of methane trisulphonate as the catalyst in an organic solvent. The product of the process is the most active and industrially most important member of the vitamin E group.

21 Claims, No Drawings

MANUFACTURE OF α-TOCOPHEROL

This application is the National Stage of International Application No. PCT/EP2003/010837, filed Sep. 30, 2003.

The present invention is concerned with a novel process for the manufacture of (all-rac)-α-tocopherol by the acid-catalyzed reaction of trimethylhydroquinone (TMHQ) with isophytol (IP) or phytol (PH) in a solvent. As is known, (all-rac)-α-tocopherol (or as it has mostly been denoted in the prior art, "d,l-α-tocopherol") is a diastereoisomeric mixture of 2,5,7,8-tetramethyl-2-(4',8',12'-trimethyl-tridecyl)-6-chromanol (α-tocopherol), which is the most active and industrially most important member of the vitamin E group.

Many processes for the manufacture of "d,l-α-tocopherol" (referred to as such in the literature reviewed hereinafter) by the reaction of TMHQ with IP or PH in the presence of a catalyst or catalyst system and in a solvent or solvent system are described in the literature. These processes go back to the work of Karrer et al., Bergel et al. as well as Smith et al. [see Helv. Chim. Acta 21, 520 et seq. (1938), Nature 142, 36 et seq. (1938) and, respectively, Science 88, 37 et seq. (1938) and J. Am. Chem. Soc. 61, 2615 et seq. (1939)]. While Karrer et al. carried out the synthesis of d,l-α-tocopherol from TMHQ and phytyl bromide in the presence of anhydrous zinc chloride ($ZnCl_2$; a Lewis acid), not only Bergel et al. but also Smith et al. used TMHQ and PH as starting materials. In the following years mainly modifications, e.g. alternative solvents and Lewis acids, were developed. From the work of Karrer et al. there was developed in the year 1941 a technically interesting process for the manufacture of d,l-α-tocopherol which was based on the reaction of TMHQ with IP in the presence of the catalyst system $ZnCl_2$/hydrochloric acid (HCl) (U.S. Pat. No. 2,411,969). Later publications, e.g. Japanese Patent Publications (Kokai) 1985/054380, 1985/064977 and 1987/226979 [Chemical Abstracts (C.A.) 103, 123731s (1985), C.A. 103, 104799d (1985) and, respectively, C.A. 110, 39217r (1989)], describe this reaction in the presence of zinc and/or $ZnCl_2$ and a Brönsted (protonic) acid, such as a hydrohalic acid, e.g. HCl, trichloroacetic acid, acetic acid and the like, especially $ZnCl_2$/HCl, as the catalyst system. Disadvantages of these and further published processes featuring $ZnCl_2$ in combination with a Brönsted acid are the corrosive properties of the acids and the contamination of the waste water with zinc ions as a result of the large amount of $ZnCl_2$ required for the catalysis.

The manufacture of d,l-α-tocopherol by the reaction of TMHQ with phytyl chloride, PH or IP in the presence of boron trifluoride ($BF_3$) or its etherate ($BF_3.Et_2O$) is described in German Patents 960,720 and 1,015,446 as well as in U.S. Pat. No. 3,444,213. However $BF_3$ too has corrosive properties.

Also, the reaction of TMHQ with IP or PH in the presence of a Lewis acid, e.g. $ZnCl_2$, $BF_3$ or aluminium trichloride ($AlCl_3$), a strong acid, e.g. HCl, and an amine salt as the catalyst system is described in European Patent Publication (EP) 100,471. In an earlier patent publication, DOS 2,606,830, the IP or PH is pretreated with ammonia or an amine before the reaction with TMHQ in the presence of $ZnCl_2$ and an acid is effected. In both cases corrosion problems occur.

A further interesting method for the manufacture of d,l-α-tocopherol from TMHQ and IP comprises using an isolated TMHQ-$BF_3$ or —$AlCl_3$ complex and a solvent mixture featuring a nitro compound (DOS 1,909,164). This process avoids to a large extent the formation of undesired by-products because it involves mild reaction conditions. The yield of d,l-α-tocopherol from a process using IP and the solvent mixture methylene chloride/nitromethane is given as 77%. However, the use of such a solvent mixture is disadvantageous.

The manufacture of d,l-α-tocopherol by the reaction of TMHQ with IP using cation exchange resin complexes of metal ions ($Zn^{2+}$, $Sn^{2+}$ and $Sn^{4+}$) is disclosed in Bull. Chem. Soc. Japan 50, 2477–2478 (1977); amongst other disadvantages it gives the product in unsatisfactory yields.

The use of macroreticular ion exchangers, e.g. Amberlyst® 15, as the catalyst for the reaction of TMHQ with IP is described in U.S. Pat. No. 3,459,773. However, the d,l-α-tocopherol could not be obtained in the requisite purity.

EP 603,695 describes the manufacture of d,l-α-tocopherol in liquid or supercritical carbon dioxide by the reaction of TMHQ with IP or PH in the presence of acidic catalysts, such as $ZnCl_2$/HCl and ion exchangers. The reported yields are unsatisfactory.

The reaction in the presence of a catalyst system which consists of iron(II) chloride, metallic iron and HCl gas or aqueous solution is described in DOS 2,160,103 and U.S. Pat. No. 3,789,086. The formation of less by-products is advantageous compared with the aforementioned process using $ZnCl_2$/HCl. However, corrosion problems and chloride contamination are equally disadvantageous.

An interesting alternative for the reaction of TMHQ with IP to d,l-α-tocopherol comprises using trifluoroacetic acid or its anhydride as the catalyst (EP 12824). Although in this process the avoidance of HCl is achieved, the catalyst is relatively expensive.

The use of the heteropoly acid 12-tungstophosphoric or 12-tungstosilicic acid as the catalyst for the reaction of TMHQ with IP was described for the first time in React. Kinet. Catal. Lett. 47(1), 59–64 (1992). d,l-α-Tocopherol could be obtained, using various solvents, in about 90% yield.

A further process described in the literature [EP 658,552; Bull. Chem. Soc. Japan 68, 3569–3571 (1995)] for the synthesis of d,l-α-tocopherol is based on the use of a various lanthanide trifluoromethanesulphonates (triflates), e.g. scandium trifluoromethanesulphonate, as the catalyst for the reaction. With up to about 10% excess of IP this process gives yields up to 98%.

The use of ion-exchanged bentonite, montmorillonite or saponite through treatment with e.g. scandium chloride and other metal salts (yttrium, lanthanum, etc.) as the catalyst for the reaction of TMHQ with IP or PH has as a disadvantage the need for a large amount of catalyst [EP 677,520; Bull. Chem. Soc. Japan 69, 137–139 (1996)].

According to the Examples of EP 694,541 the reaction of TMHQ with IP to α-tocopherol can be achieved in high yields and with a high product purity when such solvents as carbonate esters, fatty acid esters and certain mixed solvent systems are employed, the exemplified catalysis being effected by $ZnCl_2$/HCl. Disadvantages in this process are, in addition to the contamination of the waste water by zinc ions, the usual large "catalyst amount" of $ZnCl_2$ used.

According to WO 97/28151 the acid-catalyzed reaction of TMHQ with IP can be performed in a cyclic carbonate or α-lactone as the solvent. The preferred catalyst is a mixture of orthoboric acid and oxalic, tartaric or citric acid, or boron trifluoride etherate.

WO 98/21197 describes the manufacture of d,l-α-tocopherol from TMHQ and IP using bis(trifluoromethylsulphonyl)imide or a metal salt thereof optionally together with a strong Brönsted acid, as catalyst in such types of aprotic solvents as aliphatic and cyclic ketones or esters, and aromatic hydrocarbons.

Using the same kind of bis(trifluoromethylsulphonyl) imide catalyst it has been shown in EP 1,000,940 that the d,l-α-tocopherol manufacturing process can also be realized in supercritical carbon dioxide or nitrous oxide as the solvent.

From the foregoing review it is evident that most of the previously known processes have considerable disadvantages. Thus, corrosion problems occur in all processes in which such acid catalysts as boron trifluoride are used. Toxicity problems with the boron trifluoride adducts also occur, and when iron or zinc is used there is a contamination of the waste water with the metal ions which is today no longer acceptable. In some processes the formation of undesired by-products, e.g. phytyltoluenes, chlorophytols, and products of the dehydration of IP or PH, i.e. so-called phytadienes, is an especially serious problem: the selectively of the reaction is unsatisfactory. In most cases the yields are unsatisfactory.

The object of the present invention is to provide a process for the manufacture of (all-rac)-α-tocopherol by the reaction of trimethylhydroquinone with isophytol or phytol in the presence of a catalyst and in a solvent which does not have the disadvantages of previously known procedures. In this respect, it is necessary that the catalyst used has no, or at least a much reduced, corrosive action, is non-toxic, does not contaminate the environment, e.g. with chlorinated by-products or heavy metal ions, and catalyzes the desired reaction as selectively as possible, with as little as possible co-production of such by-products as phytadienes, and in high yields. Furthermore, the catalyst should display its activity in small, really catalytic, amounts and should be readily separable and re-usable several times.

This object of the present invention is achieved by carrying out the reaction of trimethylhydroquinone with isophytol or phytol in the presence of methane trisulphonate, of the formula $CH(SO_3H)_3$, as the catalyst in an organic solvent.

Accordingly, the present invention is concerned with a process for the manufacture of (all-rac)-α-tocopherol by the acid-catalyzed reaction of trimethylhydroquinone with isophytol or phytol, which process is characterized by carrying out the reaction in the presence of methane trisulphonate as the catalyst in an organic solvent.

Methane trisulphonate, the compound used as the catalyst in the process of the present invention, is a known compound and can be prepared from acetone or acetanilide in oleum, as described in e.g. J. Prakt. Chem. 336, 373–374 (1994). The acidity of this and further alkane polysulphonates is discussed in Z. Naturforsch. 51b, 1691–1700 (1996): see compound 24 in Table II therein.

In principle are all types of solvents useable for Friedel-Crafts reactions can be used as the solvents in the process of the present invention. In particular, however, polar aprotic organic solvents are suitably used, such as dialkyl and alkylene carbonates, e.g. dimethyl and diethyl carbonate, and ethylene, propylene and 1,2-butylene carbonate, respectively; aliphatic esters, e.g. butyl acetate; aliphatic ketones, e.g. diethyl ketone; and lactones, e.g. γ-butyrolactone; and mixtures of two or more of such solvents. Most preferred are biphasic solvent systems comprising on the one hand a polar aprotic organic solvent and on the other hand a non-polar aprotic organic solvent, examples of the latter being above all aliphatic hydrocarbons, particularly alkanes. Especially preferred such biphasic solvent systems are those comprising ethylene carbonate or propylene carbonate or 1,2-butylene carbonate, or a mixture of two or all three of these polar aprotic organic solvents, as the one (polar aprotic organic solvent) phase, and hexane, heptane or octane as the other (non-polar aprotic organic solvent) phase, especially ethylene carbonate and heptane, propylene carbonate and heptane, and a mixture of ethylene and propylene carbonate and heptane.

The amount of the methane trisulphonate catalyst is conveniently about 0.01 mole % to about 0.1 mole %, preferably about 0.0125 mole % to about 0.08 mole %, of the amount of educt trimethylhydroquinone or isophytol/phytol, whichever is in the lesser molar amount, generally the isophytol or phytol.

The process is conveniently effected at temperatures from about 80° C. to about 160° C., preferably from about 90° C. to about 150° C., especially from about 100° C. to about 142° C.

Furthermore, the molar ratio of trimethylhydroquinone to isophytol or phytol is conveniently about 1.25:1 to about 2.2:1, preferably about 1.5:1 to about 2:1.

If the process is carried out in a biphasic solvent system, especially one consisting of a polar aprotic organic solvent, such as and as preferred, a cyclic carbonate, e.g. ethylene carbonate, propylene carbonate, 1,2-butylene carbonate or a mixture of two or all three of these cyclic carbonates, and a non-polar aprotic organic solvent such as an aliphatic hydrocarbon, e.g. hexane, heptane or octane, then the volume ratio of the non-polar solvent to the polar solvent is conveniently in the range from about 1:10 to about 5:1, preferably 1:3 to about 5:1, most preferably from about 1:1.25 to about 2:1. Moreover, when mixtures comprising ethylene carbonate and propylene carbonate are used for the one phase, the volume ratio of ethylene carbonate to propylene carbonate is suitably in the range of about 1:100 to about 100:1. preferably about 1:10 to about 10:1, most preferably about 1:1.

Conveniently about 0.5–2 ml, preferably about 0.75–1.25 ml, most preferably about 0.9–1.1 ml, of a polar aprotic organic solvent are used per mmol of trimethylhydroquinone.

The process is conveniently carried out under an inert gas atmosphere, preferably gaseous nitrogen or argon.

The actual reaction generally lasts for about 0.5 to about 2.5 hours, preferably about 0.75 to 1.5 hours.

The process in accordance with the invention can be carried out batchwise or continuously, and in general operationally in a very simple manner, for example by adding isophytol or phytol, as such or in solution, portionwise to a mixture of the catalyst, the trimethylhydroquinone and the solvent, e.g. the biphasic solvent system. The catalyst can be added in solid form or, preferably, as an aqueous solution. The rate at which the isophytol or phytol is added is not critical. Conveniently, isophytol or phytol, preferably as such, is added continuously over a period from about 5 minutes to about 1 hour, preferably from about 10 to 30 minutes. After completion of the isophytolphytol addition and an appropriate subsequent reaction period the working-up can be effected by procedures conventionally used in organic chemistry.

If desired, the obtained (all-rac)-α-tocopherol can be converted into its acetate, succinate, poly(oxyethylene)succinate, nicotinate and further known application forms by standard procedures [see, for example, the 5$^{th}$ Edition of Ullmann's Encyclopedia of Industrial Chemistry, Vol. A 27, pages 484–485 (VCH Verlagsgesellschaft mbH, D-69451 Weinheim, 1996)].

The process in accordance with the invention enables the catalyst used to be separated readily and to be reused several times. Further advantages in the use of the catalyst in the process are the high yields of the process product (all-rac)-α-tocopherol, the avoidance of corrosion, the avoidance of waste water contamination with heavy metal ions, the high selectivity as well as the enabled ready isolation of the produced (all-rac)-α-tocopherol from the mixture after reaction.

The process in accordance with the invention is illustrated by the following Example:

EXAMPLE 1

7.55 g (50 mmol) of trimethylhydroquinone (purity 99.7%), 40 g of ethylene carbonate (or propylene carbonate) and 50 ml of heptane were introduced into a 200 ml four-necked flask equipped with a reflux condenser, a water separator, a mechanical stirrer and an argon gasification means and heated to reflux temperature (bath temperature 140° C.) under an argon atmosphere. After the addition of methane trisulphonate as an aqueous solution (for 0.05 mole % of $CH(SO_3H)_3$ based on the molar amount of subsequently added isophytol 4.23 mg=391 μl of catalyst were used), 12.026 ml (33 mmol) of isophytol were added at a rate of 0.6 ml/minute. Thus the volume ratio of trimethylhydroquinone to isophytol was about 1.5:1. Thereafter the heptane was distilled off and the mixture was heated to 125–130° C. for 30 minutes, then cooled to 80° C. 50 ml of heptane were added to the ethylene carbonate phase. The reaction mixture was stirred for a further 10 minutes at 50° C. The heptane layer was then separated and evaporated under reduced pressure to give (all-rac)-α-tocopherol as a viscous oil in a yield shown in the following Tables 1 and 2 in which EC signifies ethylene carbonate, PC signifies propylene carbonate and IP signifies isophytol:

TABLE 1

| Amount of catalyst (mole % relative to IP) | Solvent | Yield (%) |
| --- | --- | --- |
| 0.16 | EC + heptane | 98.2 |
| 0.056 | EC + heptane | 97.2 |
| 0.05 | EC + heptane | 95.3 |
| 0.05 | PC + heptane | 91.2 |

TABLE 2

| Ratio EC:heptane (g:ml) | Duration of addition of IP in minutes | Yield (%) |
| --- | --- | --- |
| 10:80 | 20 | 99.2 |
| 10:80 | 60 | 97.7 |
| 20:70 | 20 | 96.1 |
| 10:50 | 20 | 92.4 |
| 20:50 | 20 | 94.5 |
| 40:50 | 20 | 95.3 |

If desired, the crude product can be converted into its acetate by standard procedures.

The invention claimed is:

1. A process for the manufacture of (all-rac)-α-tocopherol comprising carrying out an acid-catalyzed reaction of trimethylhydroquinone with isophytol or phytol in the presence of methane trisulphonate as the catalyst in an organic solvent, the amount of the methane trisulphonate catalyst being about 0.01 mole % to about 0.1 mole % of the amount of educt trimethylhydroquinone or isophytol/phytol, whichever is in the lesser molar amount.

2. A process according to claim 1, wherein the solvent is a polar aprotic organic solvent, or a mixture of two or more of such solvents, or a two-phase solvent system comprising a polar aprotic organic solvent and a non-polar aprotic organic solvent.

3. A process according to claim 2, wherein the solvent is a biphasic solvent system comprising ethylene carbonate, propylene carbonate or 1,2-butylene carbonate, or a mixture of two or all three of these polar aprotic organic solvents, as the one solvent phase, and hexane, heptane or octane as the other (non-polar aprotic organic solvent) solvent phase.

4. A process according to claim 2, wherein the solvent is a biphasic solvent system of which the volume ratio of the nonpolar aprotic organic solvent to the polar aprotic organic solvent is in the range from about 1:10 to about 5:1.

5. A process according to claim 1, wherein the amount of the methane trisulphonate catalyst is about 0.0125 mole % to about 0.08 mole % of the amount of educt trimethylhydroquinone or isophytol/phytol, whichever is in the lesser molar amount.

6. A process according to claim 1, wherein the molar ratio of trimethylhydroquinone to isophytol or phytol is about 1.25:1 to about 2.2:1.

7. A process according to claim 1, wherein the reaction is effected at temperatures from about 80° C. to about 160° C.

8. A process according to claim 1, wherein about 0.5–2 ml of a polar aprotic organic solvent are used per mmol of trimethylhydroquinone.

9. A process according to claim 1, wherein the process is carried out under an inert gas atmosphere.

10. A process according to claim 1, wherein the process is carried out batchwise or continuously, and by adding isophytol or phytol, as such or in solution, portionwise to a mixture of the catalyst, the trimethylhydroquinone and the solvent.

11. A process according to claim 2, wherein the polar aprotic organic solvent is selected from the group consisting of a dialkyl or alkylene carbonate; an aliphatic ester; an aliphatic ketone; and a lactone; and the non-polar aprotic organic solvent, if present, is an alkane.

12. A process according to claim 11, wherein the dialkyl or alkylene carbonate is selected from the group consisting of dimethyl carbonate, diethyl carbonate, ethylene carbonate, propylene carbonate and 1,2-butylene carbonate; the aliphatic ester is butyl acetate; the aliphatic ketone is diethyl ketone; the lactone is γ-butyrolactone; and the alkane, if present, is selected from the group consisting of hexane, heptane, and octane.

13. A process according to claim 3, wherein the solvent is a biphasic solvent system of ethylene carbonate and heptane, of propylene carbonate and heptane, or of a mixture of ethylene and propylene carbonate and heptane.

14. A process according to claim 4, wherein the volume ratio of the non-polar aprotic organic solvent to the polar aprotic organic solvent is in the range from about 1:3 to about 5:1.

15. A process according to claim 14, wherein the volume ratio of the non-polar aprotic organic solvent to the polar aprotic organic solvent is in the range from about 1:1.25 to about 2:1.

16. A process according to claim 6, wherein the molar ratio of trimethylhydroquinone to isophytol or phytol is about 1.5:1 to about 2:1.

17. A process according to claim 7, wherein the reaction is effected at temperatures from about 90° C. to about 150° C.

18. A process according to claim 17, wherein the reaction is effected at temperatures from about 100° C. to about 142° C.

19. A process according to claim 8, wherein about 0.75–1.25 ml of a polar aprotic organic solvent are used per mmol of trimethylhydroquinone.

20. A process according to claim 19, wherein about 0.9–1.1 ml of a polar aprotic organic solvent are used per mmol of trimethylhydroquinone.

21. A process according to claim 9, wherein the inert gas atmosphere is nitrogen or argon.

* * * * *